(12) United States Patent
Heller et al.

(10) Patent No.: US 6,393,085 B1
(45) Date of Patent: *May 21, 2002

(54) ANALYSIS SYSTEM FOR NON-DESTRUCTIVE IDENTIFICATION OF EXPLOSIVES AND CHEMICAL WARFARE AGENTS

(75) Inventors: Wolfgang Heller, Schkeuditz (DE); Boris Grigorjewitsch Titov, Nowosibirsk (RU); Gerd Arnold, Leipzig (DE)

(73) Assignee: Bruker Saxonia Analytik GmbH, Leipzig (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/173,924

(22) Filed: Oct. 16, 1998

(30) Foreign Application Priority Data

Oct. 17, 1997 (DE) .......................... 197 45 669

(51) Int. Cl.$^7$ ................................. G21G 1/06
(52) U.S. Cl. ........................ 376/158; 376/157; 376/159
(58) Field of Search ................ 376/157, 158, 376/159

(56) References Cited

U.S. PATENT DOCUMENTS

| | | | | |
|---|---|---|---|---|
| 3,832,545 A | * | 8/1974 | Bartko | 250/312 |
| 4,568,510 A | * | 2/1986 | Caldwell | 376/154 |
| 4,882,121 A | | 11/1989 | Grenier | 376/159 |
| 5,153,439 A | * | 10/1992 | Gozani et al. | 250/390.04 |
| 5,200,626 A | | 4/1993 | Schultz et al. | 250/390.04 |
| 5,293,414 A | * | 3/1994 | Ettinger et al. | 378/88 |
| 5,539,788 A | * | 7/1996 | Ruddy et al. | 376/159 |
| 5,606,167 A | * | 2/1997 | Miller | 250/390.04 |
| 5,825,030 A | * | 10/1998 | Hurwitz et al. | 250/358.1 |

FOREIGN PATENT DOCUMENTS

| | | |
|---|---|---|
| EP | 0081075 A1 | 6/1983 |
| EP | 0592225 A1 | 4/1994 |
| GB | 2182143 A | 5/1987 |
| WO | WO 91/14938 A1 | 10/1991 |

OTHER PUBLICATIONS

G. Vourvopoulos et al., A pulsed fast–thermal neutron system for the detection of hidden explosives, Nuclear Instruments and Methods in Physics Research B79 (1993) 585–588 North–Holland.

D.R. Brown et al., Cargo inspection system based on pulsed fast neutron analysis, Nuclear Instruments and Methods in Physics Research B 99 (1995) 753–756.

(List continued on next page.)

Primary Examiner—John Richardson

(57) ABSTRACT

The invention relates to an analyzer for the identification of explosives and/or chemical warfare agents, with a neutron source which causes the emission of characteristic γ quanta, whereby the analysis system consists of a mobile frame to which a neutron source and a detector as well as a holder for the object are attached, with a neutron generator which contains deuterium as the target, generates neutron pulses by periodically repeated, pulsed bombardment of the target and is controlled so that short neutron pulses are emitted and repeated periodically, whereby the detector is controlled so that in cycles it detects γ quanta promptly emitted from the object due to inelastic neutron scattering and neutron capture, within at least two consecutive temporal measurement windows, whereby the first measurement window at least partially overlaps temporally the neutron pulse and the subsequent second measurement window does not, whereby in the first measurement window γ quanta are essentially detected due to inelastic neutron scattering and in the second measurement window they are detected due to neutron capture.

26 Claims, 7 Drawing Sheets

OTHER PUBLICATIONS

G. Tumbrägel; Neutronenaktivierungsanalyse; WWD Nr. 150; 1994; pp. 1–47.

G. Musiol et al.; Kern–und Elementarteilchenphysik; VCH Weinheim 1988; Chapter 12.3.5; pp. 781–787.

Knoll, G. F., "Radiation Detection and Measurement," 2nd Ed., (John Wiley and Sons Publ.), pp. 395–398, 1989.*

Bach, P., Ma, J. J., "Chemical Weapons Detection by Fast Neutron Activation Analysis Techniques," Nucl. Instrum. Methods Phys. Res., Sect. B, B79(1–4), 605–10, 1993.*

Failey, M. P. et al., "Neutron–Capture Prompt Gamma–ray Activation Analysis for Multielement Determination in Complex Samples," Analytical Chemistry, vol. 51, No. 13, Nov. 1979.*

Rhodes, E. et al., "APSTNG: Neutron Interrogation for Detection of Nuclear and CW Weapons, Explosives, and Drugs," 4th World Neutron Radiography Conf., San Francisco, USA, May 1992.*

Alvarez, R.A. and Rowland, M.S., "Toole NDE Test Report LLNL 14–MeV Neutron Activation Group," Lawrence Livermore national Laboratory, DE91–015746, UCR-L–ID–107563, Jun. 1991.*

* cited by examiner

Fig. 3
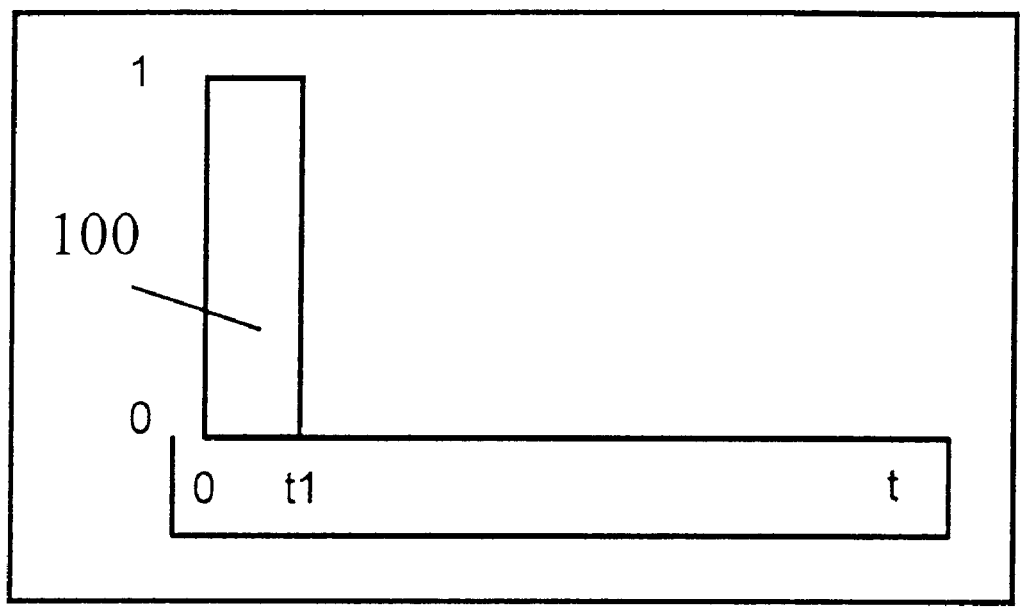
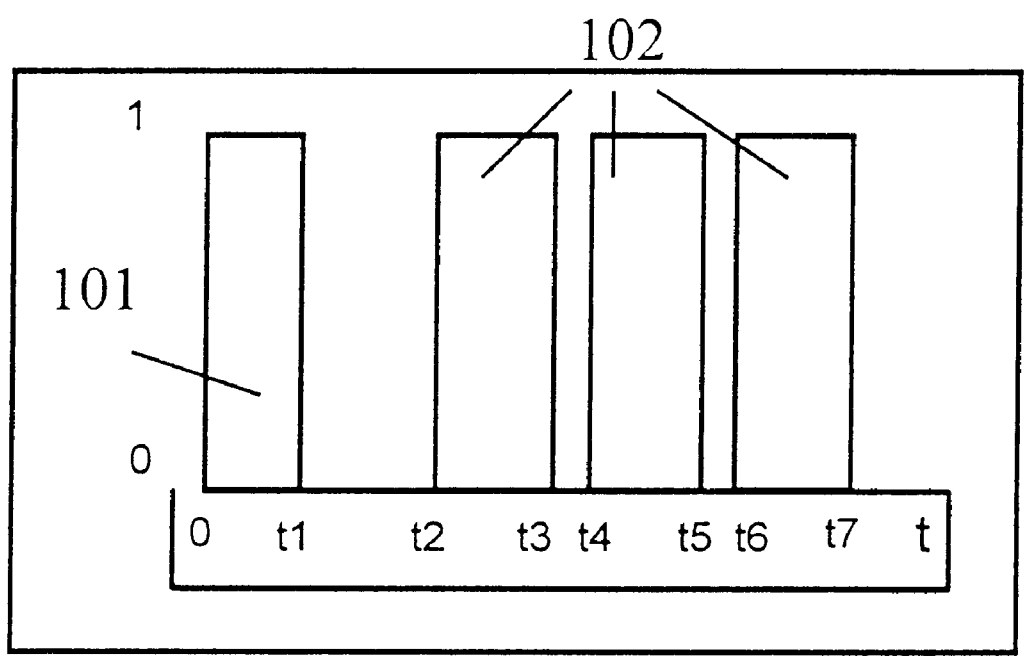

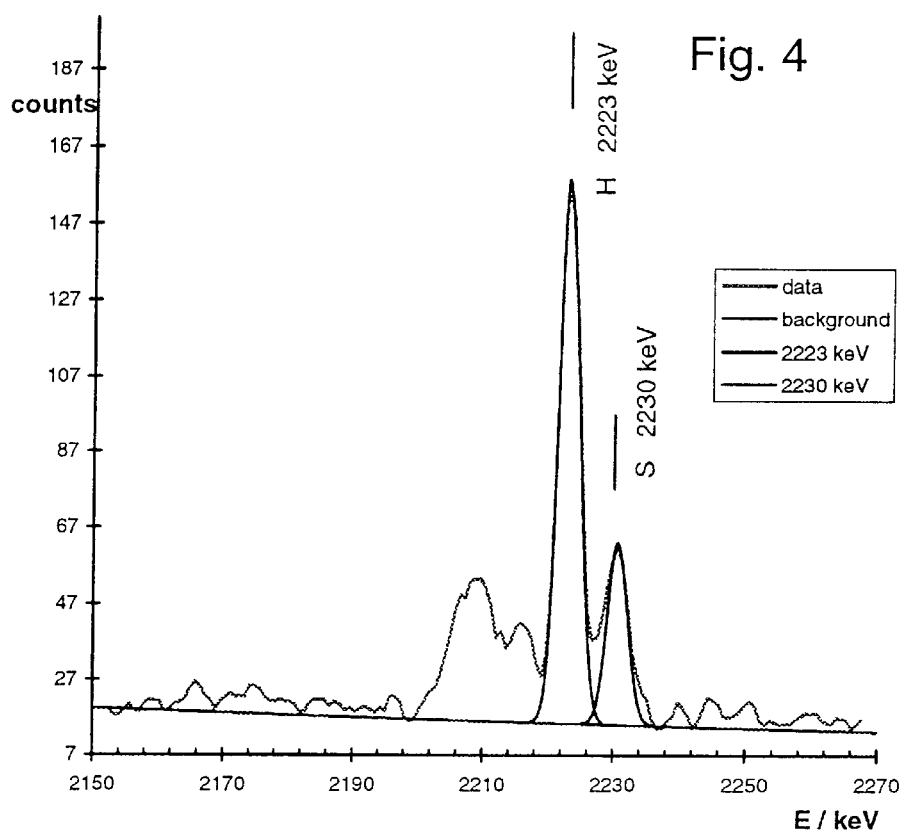
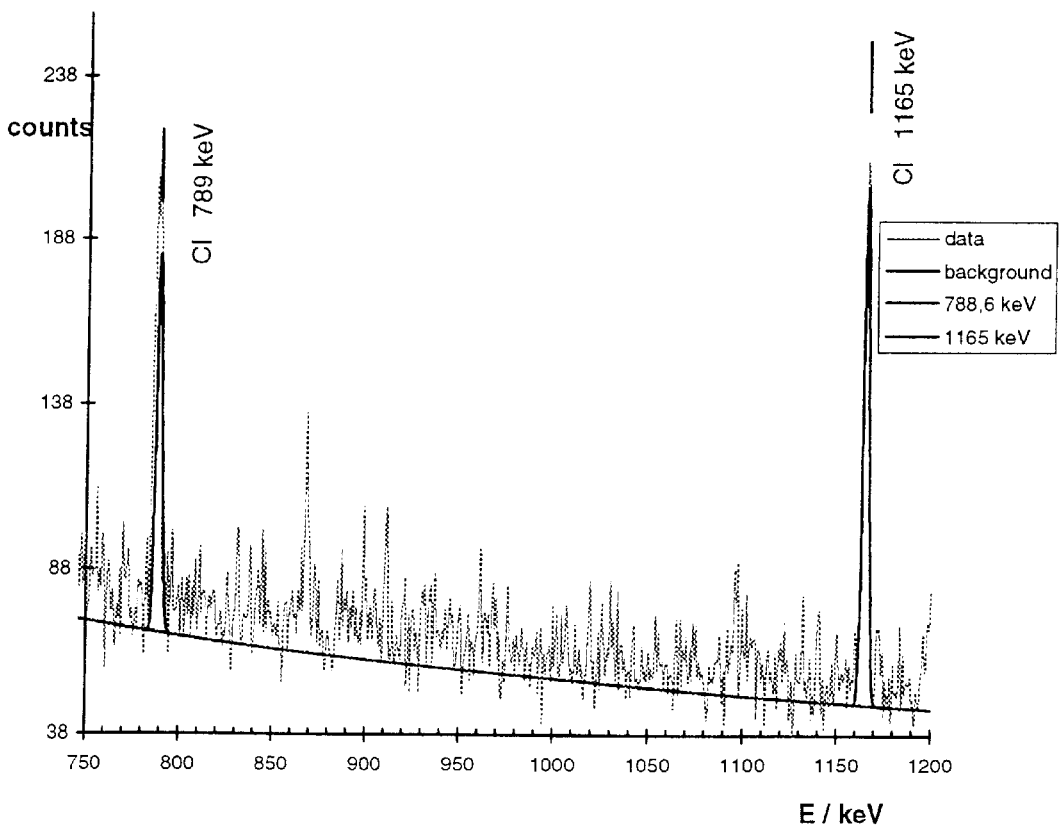
Fig. 4

ANALYSIS SYSTEM FOR NON-DESTRUCTIVE IDENTIFICATION OF EXPLOSIVES AND CHEMICAL WARFARE AGENTS

BACKGROUND OF THE INVENTION

The invention relates to an analysis system for the identification of the contents of objects, particularly explosives and/or chemical warfare agents, with a neutron source that generates neutrons which act on the object and cause the emission of characteristic γ quanta from atomic nuclei of the contents of the object, with a detector for detection of the emitted γ quanta and an electronic measuring and signal processing system for allocating the detected signals to certain atomic nuclei and for detecting certain chemical compounds which contain these atomic nuclei.

Such an analysis system is known from the publication "Neutron Activation Analysis" issued by the defense office of the German Federal Army for ABC Protection (WWD No. 150, 1994), to the entire content of which reference is made.

Particularly in connection with the worldwide problem of the disposal of chemical warfare agents and ammunition, but also the identification of explosives, methods of non-destructive analysis and identification are of very great interest.

One possible method is neutron activation analysis which can differentiate between various explosives and warfare agents, for instance, using the detected element concentrations.

In this method, a neutron source releases neutrons which penetrate the object being examined and interact with the atomic nuclei inside. Neutron activation analysis uses the γ radiation emitted due to the nuclear reaction to determine the composition of the object being examined or its contents. Due to the nuclear reaction, γ quanta of discrete energy or energies are emitted which are specific to the element atoms participating in the nuclear reaction. Due to an energy-dispersive detection of the γ quanta and corresponding evaluation of the energy spectrum, element analysis of the contents of a container, for instance, can be performed. Analysis is independent of the aggregate condition of the container contents; chemical composition (decomposition processes due to aging) or spatial separation of substances also have little or no effect on the result of measurement.

An overview of the principles of the present invention can be found in the book entitled "Kern- und Elementarteilchenphysik" (Nuclear and high energy physics) by Musiol et al. (VCH, 1988): Chapter 12.3 "Material and Process Analysis With Nuclear Radiation", particularly 12.3.5. "Activation and Excitation".

In the publication cited at the outset, it is initially explained that there are in principle two classes of neutron activation analysis (NAA): delayed classic NAA and prompt γ activation analysis (PGAA). With the first method the object is irradiated with neutrons and therefore nuclei are activated, and in a subsequent, spatially separated second step the γ radiation emitted by the activated nuclei is measured. Between these two steps there is a waiting or transport period of usually several minutes to some hours, but at least a few seconds. In one embodiment, investigated sample material is transported from the neutron source to the detector via a pneumatic tube conveyor (see FIG. 6 in the cited publication). Due to the spatial separation, one avoids direct influence of the neutron source on the detector. However, the sample becomes radioactive due to this treatment. In the second method, the γ quanta emitted directly upon neutron scatter/capture are detected in a single-stage process. This has the advantage that almost all the elements can in principle be detected because one is not dependent on unstable isotopes. However, now the source and detector must be close together, which leads to problems due to scattered radiation.

Neutron sources can certainly be any of the following: nuclear reactors; neutron generators where deuterons, for example, are shot at a target made of tritium (stationary); and isotope neutron sources (mobile). FIGS. 8a and 8b in this document show arrangements using isotope sources which are based on thermal neutron capture (8a) and inelastic neutron scattering (8b).

The described systems are either stationary and, at least as far as the source is concerned, bound to a corresponding set-up or can be mobile, but then they include a radioactive isotope source. Regular neutron generators using tritium, also use a radioactive material which is potentially very dangerous to human beings.

Particularly for mobile operation to examine objects, for example in ammunition depots, where the neutron source has to be moved by various means of transportation, any radioactive component constitutes a hazard which leads to increased expenditure on safety or renders certain applications absolutely impractical.

SUMMARY OF THE INVENTION

Therefore there is a need for a mobile analysis system of the above type where such a hazard is reduced or eliminated.

The task is solved by having the analysis system consist of a mobile frame to which the neutron source and the detector as well as the object holder are attached, the neutron source is a neutron generator which contains a deuterium target and, by periodic pulsed bombardment of the target, generates neutron pulses and can be controlled so that the neutron pulses are emitted in the energy range of 2.5 MeV from 1 μs to 1 ms duration, preferably between 20 μs and 50 μs, and are repeated at a cycle time of between 5 μs and 100 ms, the detector is controllable in such a way that it detects γ quanta promptly emitted from the object due to inelastic neutron scattering and neutron capture, in a range between 30 keV and 11 MeV within at least two consecutive temporal measurement windows in cycles, whereby the first measurement window at least partially has a temporal overlap with the neutron pulse and the following, second measurement window not, which means that in the first measurement window essentially γ quanta are detected due to inelastic neutron scattering and in the second measurement window they are detected due to neutron capture.

Due to the attachment of the source and detector to a common frame the system can be made mobile and compact. Use of a pulsed neutron generator with a deuterium target ensures that no radioactive materials are present and the system does not constitute any hazard when the generator is switched off. Utilization of prompt γ activation analysis (PGAA) makes it feasible for practically no radioactive isotopes to be generated in the object being examined and so it remains safe for subsequent handling. Signal reception in two measurement windows, which largely correspond to the two processes taking place, increases the selectivity and accuracy of identification and reduces total measuring time.

Attention must be drawn to the fact that, despite the second-window detection, which is delayed in the micro- to millisecond range, analysis is still PGAA. The delay results from several upline inelastic scattering processes which reduce the neutron energy so that neutron capture is made possible. In the energy spectrum of the first detection window, γ lines which correspond to inelastic neutron scattering tend to dominate, while in the second detection window it is the γ emission lines which dominate after neutron capture. Therefore, the γ spectra can be evaluated separately according to the types of nuclear reaction. Consequently, superpositions of energy lines made up of different types of nuclear reaction are largely avoided and particularly the γ spectra of the second detection window have a low γ background. Line allocation, peak area calculation and therefore determination of the involved types of nucleus can be advantageous. Typically, for examination of an object there is an accumulation over very many measuring cycles (in the ms range), so total measuring times of minutes can result. Obviously, the measurement can be automatic or semiautomatic. In particular, abort criteria can be written into the software as soon as adequate reliability of the identification result is achieved.

It is advantageous if there is a shield against direct γ radiation between the neutron generator and the detector. This eliminates scattered radiation which would otherwise constitute a problem due to the close proximity. It has become evident that for the intended purposes a shield made of tungsten is most suitable. Apart from the direct admission of γ radiation to the detector, neutrons which can pass directly from the source into the detector can also cause interference. It is therefore also preferable to provide a shield against such neutrons, for instance in the form of small cadmium plates. Since γ quanta can certainly be generated again in cadmium, it is particularly preferable if the cadmium plates are for the most part completely surrounded by tungsten, which therefore also protects the detector against the γ radiation resulting in the cadmium.

Preferably, the detector is a solid state detector (HPGe) with cooling, particularly by coupling to a bath of cryogenic liquid such as nitrogen or by means of a refrigerator. A Peltier cooling system can in principle also be used.

Due to the development of reliable compact coolers, the utilization of electrically driven refrigerators would seem particularly advantageous. The cooled solid state detectors have a much better resolving power than scintillation detectors.

The detector is connected to an electronic amplifier unit with, for example, preamplifier, main amplifier and ADC, a four-channel analyzer, and a computer (PC) with evaluation software for peak analysis of the recorded γ spectra. The computer can also handle the controlling of the entire measuring procedure, i.e. it can essentially control pulse length, cycle times, total measuring time, amplifier settings, etc.

The computer memory device contains the peak positions and other parameters of set elements for the relevant nuclear processes. Preferably, analysis of the measured γ spectra uses at least two of the following elements: hydrogen, nitrogen, aluminum, fluorine, phosphor, sulfur, chlorine, or arsenic, which are characteristic of many chemical warfare agents or explosives.

It is particularly advantageous that the frame of the mobile analysis system includes devices for adjusting the neutron generator and the detector. In this way it is always possible in a compact unit to set the best geometry for the intended measurement. It is also preferable if the shielding and/or sampling are adjustable.

The frame, electronics and detector cooling should preferably be accommodated, at least partially, in a common housing. The computer may also be integrated in the housing, but connection of an external laptop computer is also a useful alternative. All this leads to a compact, robust and mobile unit which, without any major difficulties, can be taken to various sites in the field by any means of transportation.

Apart from the shield between the neutron source and the detector, the analyzer can include a shield to protect operating personnel against neutrons and γ radiation. This makes it possible for the personnel to be close to the unit during the current measurement.

The examined objects should preferably be metal-cased containers (warfare agents), grenades, bombs, or the like. The entering neutrons and the emitted γ quanta penetrate the metal case.

It is evident that the features described above and those listed below can not only be used in the mentioned combination but also in any other combination or on their own, without abandoning the scope of the invention.

The invention will be explained in more detail using the embodiments and figures. The figures are as follows:

BRIEF DESCRIPTION OF THE DRAWINGS

FIG. 3: Pulse diagram of the neutron generator and the detection;

FIG. 4: γ spectrum of a mustard gas simulation substance; a) inelastic scattering, b) neutron capture;

DETAILED DESCRIPTION OF THE INVENTION

Figure 1:
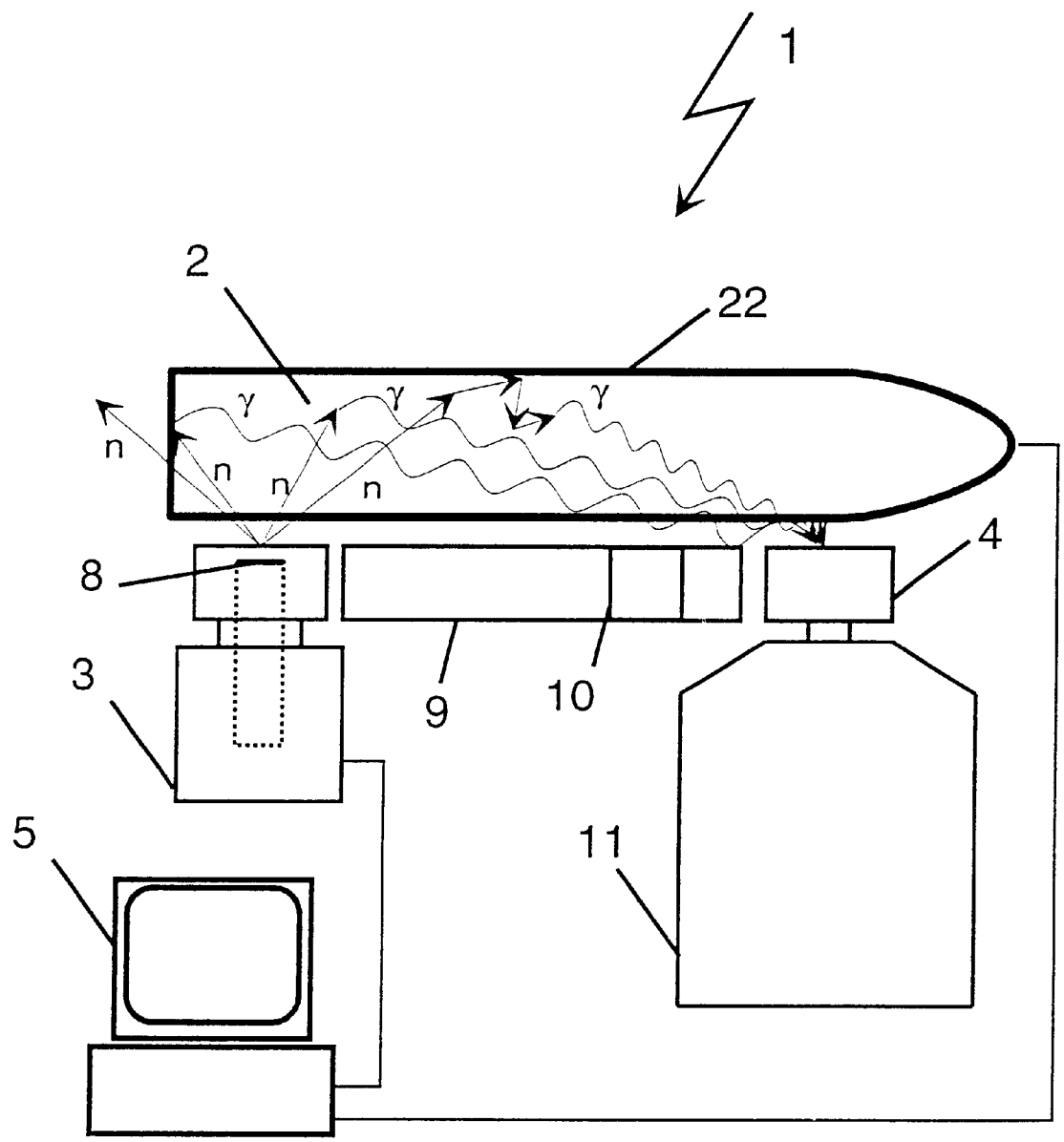
FIG. 1: Schematic diagram of the components of an embodiment of an analyzer based on the invention.

FIG. 1 shows extremely schematically an analysis system 1 which essentially comprises four components: a neutron source 3, a γ radiation detector 4 with evaluation electronics 5, shielding devices 9 and 10. Retaining and adjusting devices 6, 7, 12, and 13 have been left out of FIG. 1 for simplicity's sake.

Neutron source 3 is designed as a neutron generator in which a deuteron beam hits a deuterium-containing target 8, where it releases neutrons which are emitted from the target, essentially isotropically, with an energy of approx. 2.5 MeV. Due to the use of deuterium instead of the otherwise usual tritium, neutron source 3 contains no radioactive material. The emitted neutrons penetrate case 22 of an object 2 and are scattered inelastically by the atomic nuclei inside object 2 or, possibly after several scattering processes, absorbed. In both cases the atomic nuclei concerned emit characteristic γ radiation in the range between 100 keV and approx. 11 MeV, which is detected by a γ detector 4 (e.g. HPGe). Detector 4 is thermally coupled to a cooling system 11, which keeps it at approximately the temperature of liquid nitrogen. To keep direct γ radiation or neutron radiation away from detector 4, shields 9 and 10 are positioned between source 3 and detector 4. They are made of tungsten blocks 9, which surround cadmium plates 10. Downline of detector 4 there is an electronic measurement and evaluation unit 5, which processes the signal received from detector 4 by energy dispersion turning them into a spectrum. Due to the use of fast amplifiers and ADC, counting losses are kept to a minimum. Electronic unit 5 can also include an evaluation computer which can then also control the pulse sequences of neutron generator 3. However, as an alternative, a portable (laptop) computer can be used at some distance from analyzer 1.

Figure 2:
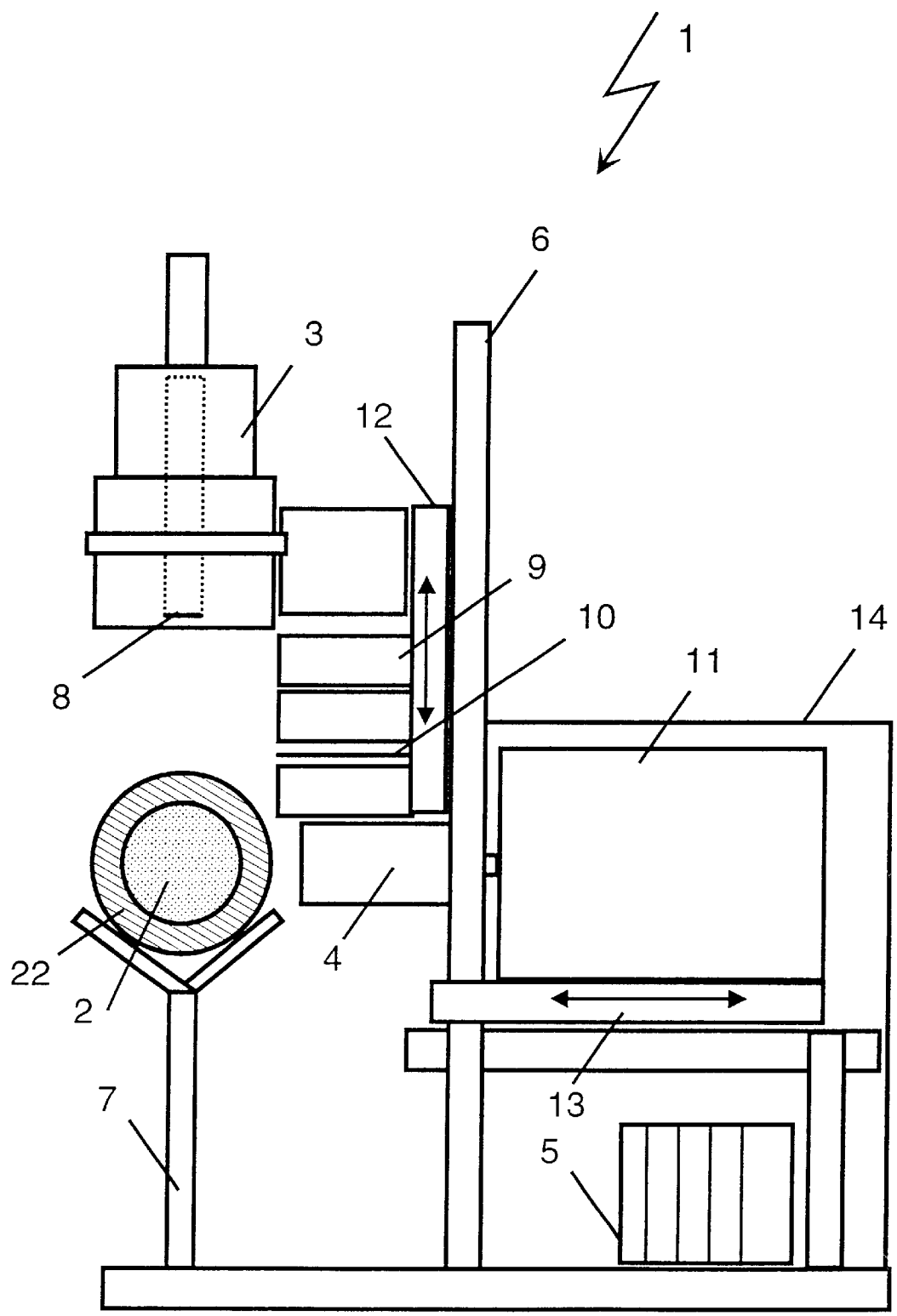
FIG. 2: Schematic diagram of an embodiment of an analyzer based on the invention.

FIG. 2 shows a schematic diagram of the geometric arrangement of the components of analyzer 1. Neutron generator 3, detector 4 and a holder 7 for test object 2 are attached to a common frame 6. Adjusting devices 12 and 13 ensure that neutron source 3 and the detector 4 can be moved along several axes relative to object 2. This adjustment option permits optimization of the geometry of the arrangement with regard to signal strength and stray radiation. In addition, it can be adapted to different objects 2. Optionally, parts of shields 9 and 10 can also be adjustable or can be replaceable. Apart from the preferred materials tungsten and cadmium, lead and $^6$Li or a combination of polyethylene and boron can be used, for instance. Parts of the common frame 6, electronics unit 5 and cooling system 11 are accommodated in a housing 14.

The number of nuclear reactions of an element depends on the neutron flux, the interaction cross sections of the element atomic nuclei and the concentrations in the substance being investigated. The interaction cross sections differ very much, not only from element to element, they also depend considerably on the neutron energy.

Due to the large number of different interactions, mutual influencing and disturbances occur. A solution to the problem is the pulsed operation of the neutron generator and the recording of the γ spectra in measurement windows during and after pulsed excitation. FIG. 3 shows a schematic representation of the measuring principle. The upper part shows a neutron pulse 100 between relative times 0 and t1, which is repeated periodically. Typical pulse lengths are in the region of several microseconds and the repetition times are a few milliseconds. The lower part shows the measurement windows 101 and 102, during which signals from the detector can be recorded. The first detection window 101 in the illustrated cycle coincides temporally with neutron pulse 100 in each case. Generally speaking, there is at least one temporal overlap range between time windows 100 and 101. The first measurement interval 101 is followed by one or more further measurement windows 102, which do not overlap temporally with neutron pulse 100. In the first measurement interval 101 it is chiefly γ quanta which are detected due to inelastic neutron scattering. During the subsequent one 102 they are essentially detected by neutron capture when the neutron concerned has already been scattered inelastically. The energy windows for the respective γ radiation to be detected can be selected accordingly, particularly if the presence of certain substances has to be specifically confirmed.

FIG. 4 shows the spectrum of the mustard gas simulation substance obtained in this way and the characteristic γ lines of hydrogen, sulfur and chlorine (2) which are identified by the identification software stored in the computer. The upper spectrum stems from the first measurement window 101 and is based on inelastic neutron scattering on sulfur nuclei and the lower one is from a further one 102. It is based on neutron capture by chlorine nuclei with subsequent emission of two characteristic lines. The wall thickness of the iron container 22 was 15 mm.

Figure 5:
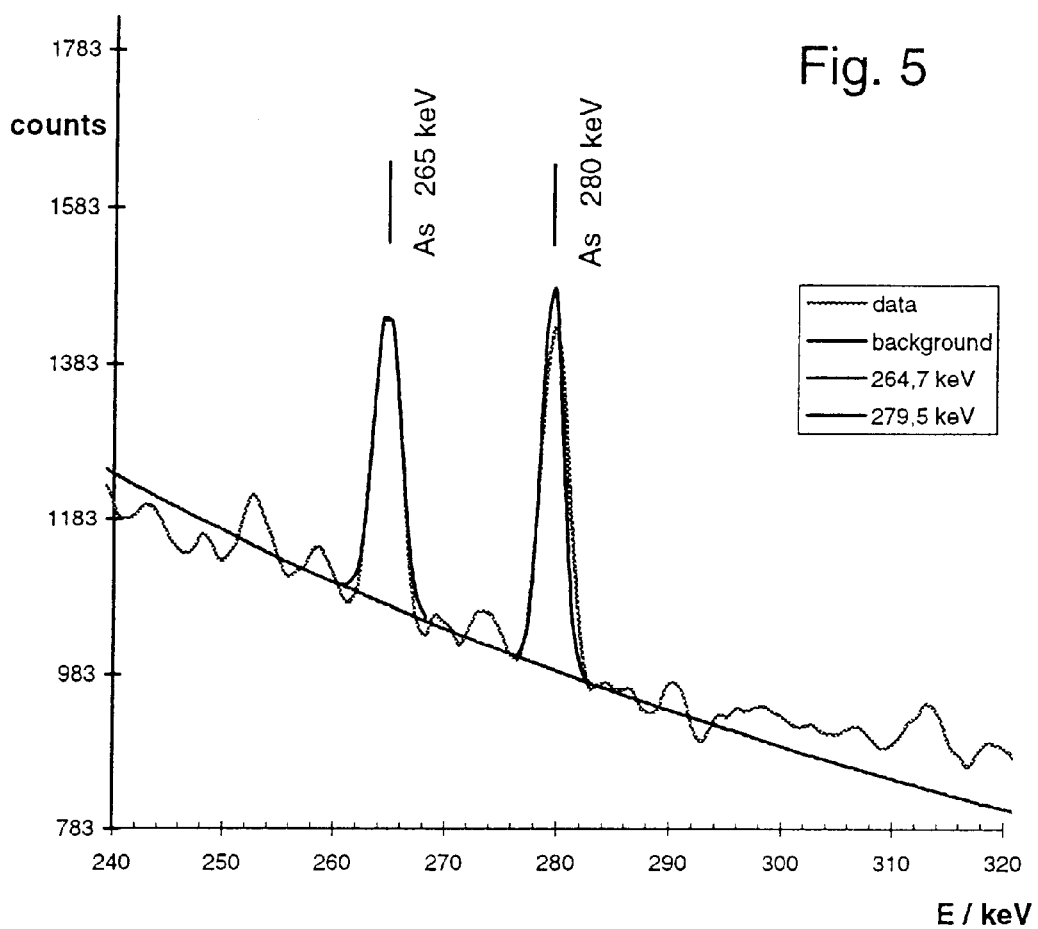
FIG. 5: Section of a lewisite γ spectrum with arsenic peaks; inelastic scattering.
Figure 6:
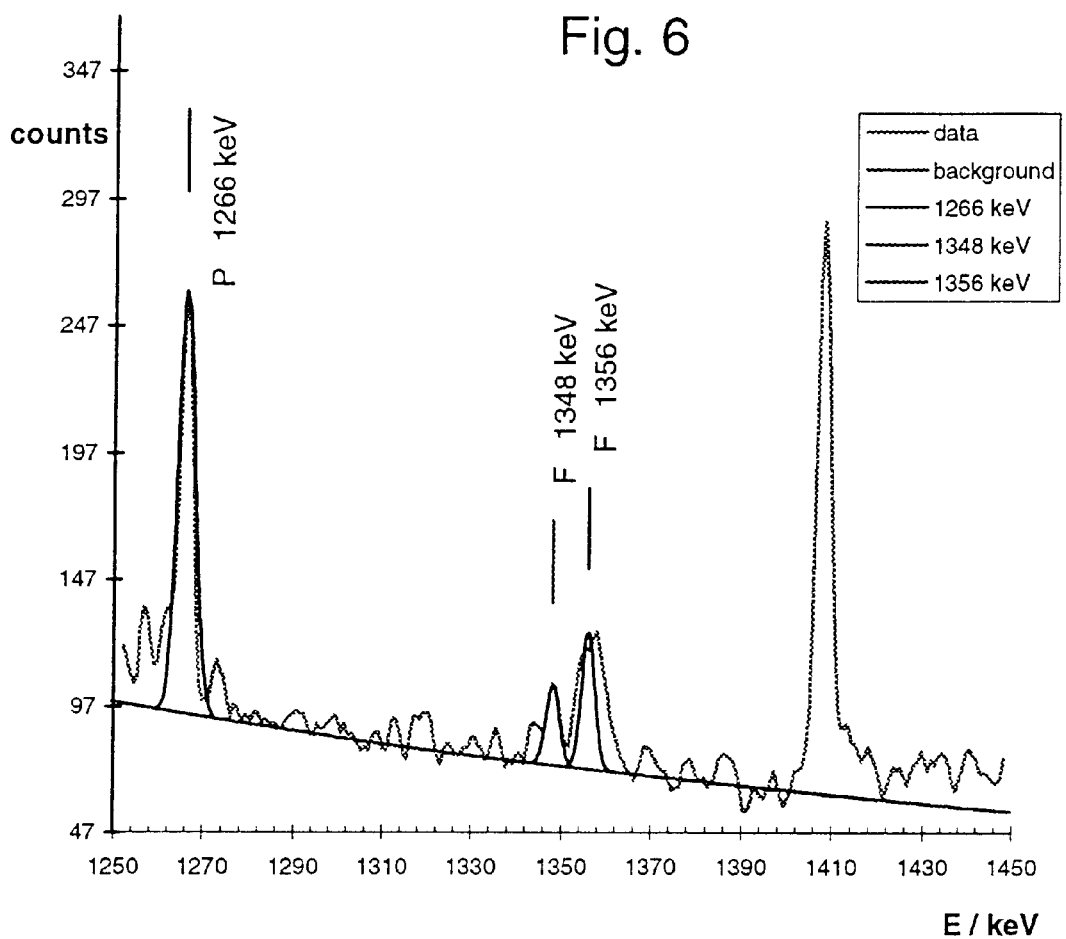
FIG. 6: Section of a sarin γ spectrum with phosphor and fluorine peaks; inelastic scattering.

In FIGS. 5 and 6, the characteristic peaks of arsenic (2) for lewisite (simulation mixture) and phosphor and fluorine (2) from sarin (simulation mixture) were identified, each in the first detection window 101. Here the wall thickness of the container was 10 mm steel in each case.

These examples demonstrate in which way substance detection takes place. The presence or absence of key elements leads to typical patterns in the γ spectrum. By analyzing certain energy regions of the γ spectra the software can decide which substance is in the container.

Figure 7:
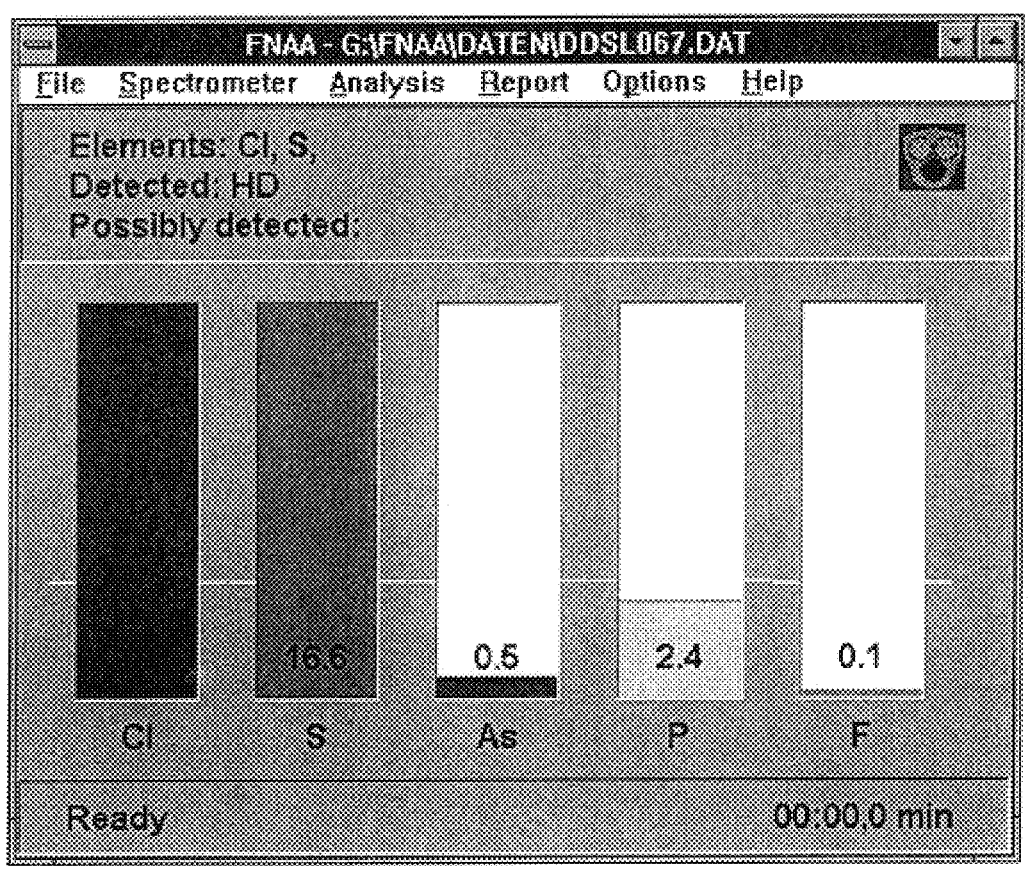
FIG. 7: Monitor screen for spectrometer control and graphic representation of the measurement results.

On the PC monitor, a graph shows the result of measurement and analytical calculations (FIG. 7). For each key element a bar is displayed which, when a threshold is exceeded, indicates that the element was detected. These identified elements are indicated on the top lines of the graph. At the same time, the substance determined thereby is stated. A special symbol at the top right-hand corner gives a warning if a chemical warfare agent was detected.

Evaluation of the γ spectra and indication of the results takes place during measurement. The data can be saved and therefore analysis can also be performed at any time after the current measurement.

We claim:

1. An analysis system for the identification of certain contents of an object, the analysis system comprising:

a neutron source that contains no radioactive material and that generates neutrons exclusively from a deuteron beam hitting a deuterium target material, such that neutrons leave the target material with an energy of approximately 2.5 MeV, the 2.5 MeV neutrons acting on the object and causing the emission of characteristic γ quanta from atomic nuclei of said contents of the object, the neutron source producing neutron pulses at a predetermined cycle time with pulse widths of less than 100 microseconds;

a measurement apparatus that detects the emitted γ quanta and attributes the detected signals to certain atomic nuclei and chemical compounds characteristic of explosives and chemical warfare agents, the measurement apparatus being configured in such a way that within a first measurement window and a second measurement window, respectively, it can detect γ quanta emitted from the object due to inelastic neutron scattering and γ quanta emitted from the object as a result of neutron capture; and a portable frame to which the neutron source and the measurement apparatus are attached.

2. The analysis system of claim 1, wherein a shield against direct γ radiation is positioned between the neutron generator and the measurement apparatus.

3. The analysis system of claim 2, wherein the shield contains tungsten.

4. The analysis system of claim 3, wherein a shield against neutrons is positioned between the neutron generator and the measurement apparatus.

5. The analysis system of claim 4, wherein the shield contains cadmium.

6. The analysis system of claim 5, wherein the shield against direct γ radiation surrounds the shield against neutrons.

7. The analysis system of claim 1, wherein the measurement apparatus has a cooling system.

8. The analysis system of claim 7, wherein the cooling system contains liquid nitrogen.

9. The analysis system of claim 7, wherein the cooling system includes an electrically driven refrigerator.

10. The analysis system of claim 1, wherein the frame comprises means for adjusting the neutron generator and the measurement apparatus.

11. The analysis system of claim 1, wherein the detected atomic nuclei include at least three of the nuclei of hydrogen, nitrogen, aluminum, fluorine, phosphor, sulfur, chlorine or arsenic.

12. The analysis system of claim 1, wherein the object is a metal-cased container.

13. The analysis system of claim 1, wherein the object is a metal-cased bomb.

14. The analysis system of claim 1, wherein the frame and other components are at least partially accommodated in a common, mobile housing.

15. The analysis system of claim 1, wherein the neutron pulses are generated by periodically repeated, pulsed bombardment of the target.

16. The analysis system of claim 15, wherein the neutron pulses are controllable so that the neutron pulses can be emitted from 1 $\mu$s to 1 ms duration.

17. The analysis system of claim 15, wherein the predetermined cycle time is between 5 $\mu$s and 100 ms.

18. The analysis system of claim 17, wherein the measurement apparatus is configured to cyclically detect $\gamma$ quanta in the range between 30 keV and 11 MeV.

19. The analysis system of claim 18, wherein the first measurement window and the second measurement window are substantially consecutive.

20. The analysis system of claim 19, wherein the first measurement window temporally overlaps with a neutron pulse, and the second measurement window does not.

21. The analysis system of claim 20, wherein during the first measurement window, $\gamma$ quanta are detected more so due to inelastic neutron scattering than due to neutron capture.

22. The analysis system of claim 21, wherein during the second measurement window $\gamma$ quanta are detected more so due to neutron capture than due to inelastic neutron scattering.

23. An analysis system for the identification of the contents of objects comprising:

a neutron source that contains no radioactive material and that generates neutrons exclusively from a deuteron beam hitting a deuterium target material such that neutrons leave the target material with an energy of approximately 2.5 MeV, the 2.5 MeV neutrons acting on the object and causing the emission of characteristic $\gamma$ quanta from atomic nuclei of the contents of the objects, the neutron source being configured to generate neutron pulses by periodically repeated, pulsed bombardment of the target, the neutron source producing neutron pulses at a predetermined cycle time with pulse widths of less than 100 microseconds;

a measurement apparatus that detects the emitted $\gamma$ quanta and attributes the detected signals to certain atomic nuclei and for detecting certain chemical compounds which contain these atomic nuclei and which are characteristic of explosive and chemical warfare agent, the measurement apparatus being configured such that in cycles it can detect $\gamma$ quanta promptly emitted from the object due to inelastic neutron scattering and neutron capture, in the range between 30 keV and 11 MeV within at least two consecutive temporal measurement windows, whereby a first measurement window temporally overlaps, at least partially, with the neutron pulse and a second measurement window does not, whereby in the first measurement window $\gamma$ quanta are detected substantially due to inelastic neutron scattering and in the second measurement window, $\gamma$ quanta are detected substantially due to neutron capture; and a mobile frame to which the neutron source and the measurement apparatus as well as a holder for the objects are attached.

24. The analysis system of claim 23, wherein the neutron pulses are emitted for a duration from 20 $\mu$s to 50 $\mu$s.

25. The analysis system of claim 23, wherein the predetermined cycle time is between 5 $\mu$s and 100 ms.

26. The analysis system according to claim 23 further comprising a shield against direct $\gamma$ radiation and a shield against neutrons each of which are positioned between the neutron generator and the measurement apparatus.

* * * * *